US012300359B2

(12) United States Patent
Schlifke

(10) Patent No.: US 12,300,359 B2
(45) Date of Patent: May 13, 2025

(54) COMPUTER-BASED METHOD FOR DETERMINING A SUNSCREEN COMPOSITION COMPRISING A PLURALITY OF UV FILTER SUBSTANCES

(71) Applicant: DSM IP Assets B.V., Heerlen (NL)

(72) Inventor: Alexander Schlifke, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 105 days.

(21) Appl. No.: 17/215,452

(22) Filed: Mar. 29, 2021

(65) Prior Publication Data

US 2021/0304851 A1    Sep. 30, 2021

(30) Foreign Application Priority Data

Mar. 30, 2020 (EP) .................................... 20166726

(51) Int. Cl.
| | | |
|---|---|---|
| *G16C 20/30* | (2019.01) | |
| *A61K 8/18* | (2006.01) | |
| *A61Q 17/04* | (2006.01) | |

(52) U.S. Cl.
CPC ................ *G16C 20/30* (2019.02); *A61K 8/18* (2013.01); *A61Q 17/04* (2013.01)

(58) Field of Classification Search
None
See application file for complete search history.

(56) References Cited

U.S. PATENT DOCUMENTS

| | | | | |
|---|---|---|---|---|
| 2004/0083083 A1* | 4/2004 | Doganaksoy | ........... | G06F 30/00 700/106 |
| 2006/0173661 A1* | 8/2006 | Kohn | ................... | G05B 13/024 703/2 |
| 2018/0060450 A1* | 3/2018 | McNamara | ............. | G06F 30/00 |

FOREIGN PATENT DOCUMENTS

| | | |
|---|---|---|
| EP | 3 208 145 A1 | 8/2017 |
| JP | 2004-158008 A | 6/2004 |
| WO | WO 2019/207129 A1 | 10/2019 |

OTHER PUBLICATIONS

Daly, S.; Ouyang, H.; Maitra, P. Chemistry of Sunscreens. In Principles and Practice of Photoprotection; Wang, S. Q., Lim, H. W., Eds.; Springer International Publishing: Cham, 2016; pp. 159-178.*

Byrd, R. H.; Hribar, M. E.; Nocedal, J. An Interior Point Algorithm for Large-Scale Nonlinear Programming. SIAM Journal on Optimization 1999, 9 (4), 877-900.*

Conte et al., "Design of Formulated Products: Experimental Component," AIChE Journal, vol. 58, No. 1, 2012, pp. 173-189, 17 pages total.

Papadopoulos et al., "Computer Aided Molecular Design: Fundamentals, Methods and Applications," Elsevier Reference Module in Chemistry, Molecular Sciences and Chemical Engineering, 2018, 77 pages total.

Grujicic et al., "Application of the Materials-by-Design Methodology to Redesign a New Grade of the High-Strength Low-Alloy Class of Steels with Improved Mechanical Properties and Processability", Journal of Materials Engineering and Performance, Jan. 2016, vol. 25, No. 1, pp. 165-178.

Herzog et al., "Simulation of sunscreen performance", Pure Appl. Chem., Oct. 1, 2015, vol. 87, No. 9-10, pp. 937-951.

Kockott et al., "New Approach to Develop Optimized Sunscreens that Enable Cutaneous Vitamin D Formation with Minimal Erythema Risk"; PLOS One, Jan. 29, 2016, vol. 11, No. 1, total 10 pages.

English translation of the Japanese Office Action for Japanese Application No. 2021-055105, dated Jul. 22, 2024.

* cited by examiner

*Primary Examiner* — Soren Harward
(74) *Attorney, Agent, or Firm* — BIRCH, STEWART, KOLASCH & BIRCH, LLP

(57) ABSTRACT

A computer-based method for determining a sunscreen composition comprising a plurality of UV filter substances, comprises the steps of selecting at least one constraint for at least one characteristic of the composition to be determined (step 30), the at least one constraint comprising a sunscreen performance target; selecting an optimization objective from a plurality of optimization objectives (step 50); and automatically determining the sunscreen composition as a composition of filter substances from a set of filter substances (step 100), the composition meeting the at least one constraint and being optimized with respect to the selected optimization objective. The automatic determination comprises the steps of generating a plurality of candidate compositions, determining a sunscreen performance of the candidate compositions using a performance simulation tool and comparing the determined sunscreen performance of the candidate compositions with the sunscreen performance target. The method allows for an automatic determination of an optimum sunscreen composition based on constraints and objectives, thus avoiding manual trial and error methods that are lengthy and do not always lead to the optimal result.

18 Claims, 2 Drawing Sheets

COMPUTER-BASED METHOD FOR DETERMINING A SUNSCREEN COMPOSITION COMPRISING A PLURALITY OF UV FILTER SUBSTANCES

TECHNICAL FIELD

The invention relates to a computer-based method for determining a sunscreen composition comprising a plurality of UV filter substances. It further relates to a computer program product for determining a sunscreen composition and to a method of preparing a sunscreen composition.

BACKGROUND ART

Today sunscreen developers have several computational tools available, which can predict the sun protection performance of a UV filter combination to some extent (cf. e. g. B. Herzog, U. Osterwalder: "Simulation of sunscreen performance", Pure Appl. Chem. 2015; 87(9-10): 937-951). Some of the tools are available online for general use (e. g. BASF® Sunscreen Simulator or DSM® SUNSCREEN OPTIMIZER™). Based on an input of a combination of UV filters they predict inter alia the sun protection factor (SPF) and the ratio between the UVA protection factors and the SPF. Therefore, these tools allow developers to quickly evaluate and compare different UV filter combinations in silico.

However, the huge number of possible options still means that the search for an optimal combination of filter factors by trial and error is cumbersome, lengthy and might not lead to the true optimum.

SUMMARY OF THE INVENTION

It is the object of the invention to create a method pertaining to the technical field initially mentioned, that allows for the efficient determination of optimal sunscreen compositions.

The solution of the invention is specified by the features of claim 1. According to the invention the computer-based method for determining a sunscreen composition comprising a plurality of UV filter substances, comprises the steps of:

a) selecting at least one constraint for at least one characteristic of the composition to be determined, the at least one constraint comprising a sunscreen performance target;
b) selecting an optimization objective from a plurality of optimization objectives; and
c) automatically determining the sunscreen composition as a composition of filter substances from a set of filter substances, the composition meeting the at least one constraint and being optimized with respect to the selected optimization objective, the automatic determination comprising the steps of:
   generating a plurality of candidate compositions,
   determining a sunscreen performance of the candidate compositions using a performance simulation tool and
   comparing the determined sunscreen performance of the candidate compositions with the sunscreen performance target.

As mentioned above, performance simulation tools for sunscreen compositions are available, cf. e. g. B. Herzog, U. Osterwalder: "Simulation of sunscreen performance", Pure Appl. Chem. 2015; 87(9-10): 937-951.

The inventive method allows for an automatic determination of an optimum sunscreen composition based on constraints and objectives, thus avoiding manual trial and error methods. As set out in more detail below, the effort for optimizing the composition of e. g. 5 or more filter substances is prohibitive for manual approaches, even if a sunscreen performance simulation tool is readily available. Integrating the performance simulation into an automatic determination, involving the determination of the performance of a plurality of candidate compositions therefore allows for the first time to systematically and truly find optima.

Having the possibility of selecting at least one constraint and an optimization objective the needs of an individual formulator may be respected. The desired solution may be tailored to his or her specific needs. As described in more detail below, the computer-based method according to the invention is fast enough on today's personal computers that an interactive work process is possible, where the user gets feedback in a reasonable time, preferably in a few seconds. This allows the user to quickly learn from the result and adjust constraints, boundaries, or the set of filter substances that are taken into account, if required and/or as desired.

Preferably, a user is requested to select the at least one constraint. This allows for a user-defined interactive process, where the constraints may be selected according to the general needs of the user as well as according to the properties of the sunscreen that shall be optimized. In a simple embodiment of the invention, the user selects a single value relating to the sunscreen performance (e. g. desired SPF). Nevertheless, instead of a target value the constraints may be provided in the form of ranges, of minimal values or of maximal values. Furthermore, target values or ranges for more than a single property relating to sunscreen performance may be provided.

Alternatively, the constraint is selected automatically, by the computer. In particular, constraints according to a fixed or variable sequence of constraints are selected in successive optimization steps in order to find the preferred sunscreen composition.

Preferably, a user is requested to select the optimization objective. This allows for a user-defined interactive process, where the objective may be selected according to the general needs of the user as well as according to the properties of the sunscreen that shall be optimized. In particular, the objective may be changed during the process in order to iteratively improve the sunscreen composition.

Alternatively, the optimization objective is selected automatically, by the computer. In particular, objectives according to a fixed or variable sequence of constraints are selected in successive optimization steps in order to find the preferred sunscreen composition.

The constraints and the objectives have a certain interrelation: As an example, the costs of the composition may be provided as a constraint (maximum value that shall not be exceeded) or as an objective (minimization of the costs). The other constraints and objectives, respectively, are appropriately chosen in each case.

Preferably, a sequence including the steps a)-c) is repeated, wherein the user iteratively adjusts the at least one constraint and/or the optimization objective. This allows for gradually improving the sunscreen composition, taking into account the information obtained from previous optimization steps. Due to the fact that using the inventive method a sunscreen composition may be determined within a few seconds if run on standard hardware an iterative process is feasible.

Alternatively, the process is designed in such a way that the desired sunscreen composition may be found in a single step and/or the adjustment of the constraint and/or optimization objective is carried out automatically, by the computer, based on the initially selected parameters and the results of the previous determination. In further embodiments, the computer automatically provides suggestions with respect to criteria for the further improvement of the composition, and the user decides whether to fully or partially follow these suggestions for the next step of the iterative process.

Preferably, the user selects an actual set of filter substances to be considered from a basic set of filter substances, i. e. from a superset. In particular, the selection is based on the user's knowledge, e. g. with respect to the properties of the available substances, and/or the availability of filter substances. This allows for more easily finding the optimum composition for the respective task at hand. Furthermore, by reducing the number of the filter substances to be taken into account, the automatic determination of the sunscreen composition may be accelerated considerably.

Alternatively, all available filter substances are considered or the selection of the actual set is done automatically, by the computer, e. g. based on a database relating to filter properties and/or availability.

In a preferred embodiment, the user provides a maximum amount of at least some of the selected filter substances, in particular of all the selected filter substances. This allows for ensuring that regulatory approved use levels are not exceeded. Furthermore, the sunscreen composition may be tailored to the user's needs.

Alternatively, maximum amounts are automatically considered, e. g. based on a database including regulatory information.

In some embodiments, the user provides a minimum amount of at least some of the selected filter substances. This allows for influencing the determination of the sunscreen composition to ensure that the user's needs are met.

Advantageously, the method includes the step of selecting at least one further constraint (in addition to the sunscreen performance target) for at least one characteristic of the composition to be determined.

Preferably, the at least one further constraint is a range or a boundary value (upper or lower limit) relating to one of the following properties:
a) total amount of filter substances;
b) amount of one or more distinct filter substances;
c) costs of the composition of filter substances;
d) weighting of the filter or the composition of filter substances;
e) eco-friendliness;
f) amount of extra solvent;
g) oil load.

In principle, the range may be infinitesimally small, i. e. correspond to a target value that is required to be met (exactly or within a predetermined general tolerance).

The weighting of a filter is a number, which may represent the price of the filter, a score how eco-friendly the filter is, a score how easy it is to formulate the filter, a score for the impact of the filter on the sensory to the sunscreen, etc. The weighting of a composition of filter substances is the sum of the weightings of individual filters multiplied with their corresponding percentages in this combination and may therefore represent e.g. the total costs of the filter combination, total sensory impact, etc.

The oil load is the sum of all filters in the oil phase plus the extra solvent, which may be required to dissolve solid filters. It is a good measure of how much freedom a formulator has with a particular filter combination, e. g. with respect to the addition of further components in the oil phase that may be relevant e. g. for the skin feel of the final product.

Eco-friendliness or ecotoxicological friendliness relates to the impact of the filter substances on the environment. Methods for determining an ecotoxicological value are described e. g. in U.S. Pat. No. 7,096,084 B2 (S. C. Johnson & Son, Inc.), U.S. Pat. No. 9,595,012 B2 (Johnson & Johnson Consumer Inc.) as well as WO 2019/207129 A1 (BASF SE).

The above list of possible constraints is not exhaustive, further constraints are possible, such as relating to sensory properties of the sunscreen composition.

Preferably, the sunscreen performance target is chosen from one of the following:
a) in vivo or in vitro Sun Protection Factor (SPF);
b) in vivo or in vitro UVA Protection Factor (UVAPF);
c) critical wavelength;
d) ratio of UVA to UVB protection; and
e) blue light protection.

The target may be provided as a target value or a target boundary (e. g. minimal value).

The in vivo or in vitro Sun Protection Factor (SPF) can be indicated as absolute SPF values, as a recommended labelled sun protection factor or as a protection category, e.g. according to the EU Commission Recommendation 2006/647/EC of 22 Sep. 2006 or other (national or multi-national) regulations with respect to the labelling of sunscreen products. Protection categories may be defined e. g. as follows:
Low protection: SPF is below 15;
Medium protection: SPF is 15 to 29;
High protection: SPF is 30 to 49;
Very high protection: SPF is over 50.

The in vivo UVA protection factor (UVAPF) can e.g. be indicated as UVAPF, determined according to ISO 24442: 2001, as UVAPF protection Grade according to the JCIA, which relates to a voluntary industry standard of the Japan Cosmetics Industry Association (JCIA) for measuring the UVA protection efficacy or as persistent pigment darkening (PPD) or immediate persistent darkening (IPD) values.

As usual, the critical wavelength denotes the wavelength at which a sunscreen allows 10% of the rays to penetrate. For example, a sunscreen with a critical wavelength of over 370 nm is considered by the FDA to provide excellent UVA protection.

The ratio of UVA to UVB protection can be given as UVAPF/SPF or the Boots Star® rating, which is a proprietary in vitro method to describe the protection offered by sunscreen products, introduced by the Boots Company in 2011.

Blue light (also often referred to as high-energy visible light (HEV light)) protection indicates the protection from light in the violet-blue spectrum on the visible spectrum, which is found in daylight but also in LED and fluorescent lighting.

In principle, the quantities relating to the sunscreen performance may be determined according to any standard as long as the used performance simulation tool is capable to provide the sunscreen performance according to this standard, i. e. the available targets may depend from the underlying simulation tool.

The above list of performance targets is not exhaustive, further targets, including suitable combinations of the above, are possible.

Preferably, the plurality of optimization objectives include at least two of the following:
a) cost efficiency;
b) weighting;
c) filtering efficiency;
d) eco-friendliness;
e) amount of extra solvent;
f) minimal oil load;
g) most homogenous protection;
h) highest sun protection factor and/or UVA protection factor;
i) highest blue light protection; and
j) similarity to a provided composition of filter substances These objectives can be minimized or maximized.

Sunscreen simulation tools facilitate a quick and easy side-by-side comparison of different filter combinations. But direct comparison of properties such as efficiency or costs are only meaningful if all the compared combinations deliver more or less the same performance. When comparing many combinations, the precise adjustment of each combination requires significant efforts.

In the context of the present invention, choosing similarity to a (user) provided composition of filter substances as an objective greatly simplifies this adjustment process. A composition of filter substances is determined that is as close as possible to the (user) provided composition but that achieves the performance target and meets the constraints. The resulting adjustment will therefore preserve the principle idea of the user as close as possible and quickly adjust the filter concentrations to meet the desired performance target and the constraints.

Preferably, in this case the objective to be minimized is the Euclidean distance between the provided composition and the determined composition, meeting the constraints.

The list of objectives is not exhaustive, further objectives, including suitable combinations of the above or sensory properties of the composition, are possible.

The huge amount of possible UV filter combinations makes a simple combinatorial brute-force approach infeasible: Assuming that an optimal combination of 6 UV filters shall be found (which is a number that is very common in the sunscreen industry), more than 15 billion possible filter combinations results when the amount of each filter is quantified with discrete increments of 0.1 weight % up to a maximum of 5.0 weight %. Additionally, there are 134'596 options to select these 6 filters from the 24 filters approved in Europe, which gives a total of about 2100 trillion possible combinations for this setup. Usual personal computers that are commercially available today, having a CPU clock frequency of typically 2-4 GHz require about 2-4 ms for the determination of a sunscreen performance of a given composition, using the performance simulation tool. Accordingly, the computing time for calculating all the performance values would amount to more than 130'000 years. Optimized code may reduce the calculation time by a factor of 100 the most and the use of multiple cores may reduce the calculation time by a factor of 8-10. Still, even when exploiting all these measures, the computing time is more than 100 years. Furthermore, an expansion to more than 6 filters, which may be desirable in order to meet all the requirements, greatly increases the computing time.

Therefore, in a first preferred embodiment, the automatic determination of the sunscreen composition comprises a numerical optimization of an objective function related to the selected optimization objective, the variables of the objective function including proportions of the filter substances of the sunscreen composition to be determined.

Numerical optimization algorithms dispense with the requirement of determining the performance for a large number of candidate compositions. They are powerful tools for finding optimal solutions in high dimensional spaces.

Advantageously, the numerical optimization comprises an application of a sequential quadratic programming method, in particular of an interior-point method.

Numerical optimization algorithms require that the constraint objective function is convex in order to find the global optimum instead of local optima. Furthermore, they are more or less sensitive to the choice of a good starting point to guarantee global convergence. There is no universal optimization algorithm but rather a collection of algorithms, each of which is tailored to a particular type of optimization problem. It is not possible to predict whether the problem may be solved rapidly or slowly and, indeed, whether the solution is found at all.

Surprisingly it has now been found that for to the optimization of sunscreen compositions numerical optimization algorithms, which evaluate the first and second derivative of the objective function for their choice of the search direction and step size taken at each iteration, are not only capable to find global solutions to the above described objectives but are also fast enough on regular personal computers to allow an interactive work process.

The complexity of current algorithms used in sunscreen performance prediction tools require the estimation of the first derivative e.g. by the finite difference method for the calculation of the Jacobian as well as Quasi-Newton methods such as BFGS or SRI to approximate the Hessian at each iteration.

When using numerical optimization for the determination of the sunscreen composition there are no limitations with respect to the number of UV filters—accordingly, a filter pre-selection is not necessary for calculation reasons. Indeed, fast calculations are possible even with more than 20 filters on regular personal computers. Furthermore, there are no resolution limits, which means that the "true optimal" composition may be found.

Nevertheless, it has to be taken into account that the numerical optimization approach might not work with all constraint objectives, i. e. it is not guaranteed that the global optimum is found for all constraint objectives. Furthermore, the result will not be rounded to a reasonable number of digits. It will be necessary to use methods such as branch and bound to obtain results on the desired resolution level (e. g. 0.1 weight % increment).

In a second preferred embodiment, for the automatic determination of the sunscreen composition a plurality of candidate compositions are automatically defined and the sunscreen performance of at least some of the plurality of candidate compositions is determined using the performance simulation tool.

Using the combinatorial approach, an optimum (or near-optimum) sunscreen composition may be found for any objective and it is guaranteed that the solution is close to the global optimum. Furthermore, a list of best solutions may be obtained without extra effort (see below).

A combinatorial approach is feasible by applying various measures to reduce the number of calculations, which are in particular:

1) Reducing the number of UV filters by a preselection of at most 6 filters by the user.
2) Choosing an increment for the amount of filters of 0.5-1.0 weight %, most preferably 0.5 weight %.

3) Reduce the search space by:
  3a) Searching for the lowest total filter amount capable to achieve the targeted performance by:
    a. Conservatively estimate the total amount of filters necessary to achieve the performance target (e.g. SPF/2 weight % of filter) and calculate only combinations with a corresponding total amount of filters (e. g. for an SPF 30, 6 filters, 312'620 calculations are required with an increment of 0.5 weight % and a maximal use level of 5 weight % per filter).
    b. Enumerate the corresponding filter combinations in a way that combinations with most of the most efficient filters are tested first.
    c. Stop the calculation as soon as the target performance is met (typically less than 1000 calculations).
    d. Re-estimate the total amount of filters according to the over or under performance of the first estimate and again calculate only combinations with a corresponding total amount of filters.
    e. Repeatedly reduce the total amount of filters by a fixed number e.g. 1 weight % and calculate again all these combinations until the target is not achievable anymore (backward search).
    f. Increase the total amount of filters by the increment (e.g. 0.5 wt %) until the performance target is achieved again (forward search). As soon as the target is achieved stop the search. This will give the lowest total filter amount (most efficient filter combination(s)) capable to achieve the target performance.
  3b) Start from the lowest feasible total filter amount and search optimal solutions by increasing the total amount by one increment for each search e.g. 0.5 wt %.

Accordingly, it is preferred that in a first substep a lowest total amount of filter substances is determined for a composition that achieves the sunscreen performance target and in a subsequent second substep a constraint on a value of the total amount of filter substances of the candidate compositions is gradually increased, starting from the determined lowest total amount, until a stop criterion is met.

As described above, preferably the lowest total amount of filter substances is determined by gradually reducing a total amount of filter substances of candidate compositions tested for their sunscreen performance until the sunscreen performance target is not reachable and by subsequently gradually increase the total amount of filter substances until the performance target is met again, wherein an increment of the gradual increase is smaller than an increment of the gradual reduction.

The determination is started with a conservative estimate for the total amount of filter substances. The candidate compositions tested in one step all have the respective total amount. If one of the candidate composition is found to meet the sunscreen performance target, the corresponding step ends and the next step with a reduced total amount follows. This is repeated until in a step no candidate composition meeting the sunscreen performance target can be found. The increments for the gradual reduction and for the gradual increase may be fixed or variable, e. g. dependent on an underperformance or overperformance of the tested compositions.

Preferably, candidate compositions to be tested are sorted according to an efficiency of comprised filter substances in such a way that candidate compositions with a high expected efficiency are tested first and that a test sequence is stopped as soon as the sunscreen performance target is met by one of the candidate compositions. This greatly reduces the number of candidate compositions to be tested in the phase of gradually reducing the total amount of filter substances.

Many objectives such as costs, extra solvent and minimal oil load normally decrease (get better) with higher total filter amount until the optimum is reached. If the total amount of filters is further increased (by imposing a constraint that the total amount of used filters equals a predetermined value), some objectives such as costs, needed extra solvent or minimal oil load will increase again (get worse). Accordingly, the stop criterion may be the increase (deterioration) of one or more of the objectives when the total amount of filter substances is increased.

Linear objective functions (e.g. most efficient or cost-efficient UV filter combinations) can be evaluated by simple dot products and therefore very efficiently calculated by matrix operations on regular computers. In these cases, all combinations can be efficiently evaluated at once followed by sequential block wise performance predictions. The current optimum within previous blocks (e.g. lowest cost) can be used to skip all performance predictions from residual combinations with worse values compared to this optimum. Typically, this allows to find the optimum with less than 3000 calculations for a given total amount of filters.

Preferably, the method includes the step of providing a list of best candidate compositions, e. g. those 10 or 20 compositions which have the highest values with respect to the optimization objective. Using the combinatorial approach, this list is obtained without extra effort. Based on the list, the user may chose the preferred composition, in particular a composition which is only close to the top value with respect to the optimization objective but which has some other property or properties that make it a better choice than the top composition on the list. Advantageously, the list not only includes the compositions and the values with respect to the objective but further relevant properties characterizing the compositions.

Compared with the numerical optimization approach, in the context of the combinatorial method it is required to pre-select filters as the maximum number of filters will usually be 6 to 7 for regular computers. Similarly, the minimum increment will be about 0.5 weight %. Still, the algorithm is slower (or needs considerably more computation power) than the numerical optimization approach.

Often, optimizing one specific property (such as e. g. efficiency) forces another property (such as e. g. costs) in an unacceptable range. Therefore, preferably, the inventive method comprises the step of optimizing a compromise within a plurality of optimization objectives, comprising the steps of providing acceptable ranges for values relating to each of the objectives, providing relative importance factors between the objectives and minimizing one of the values using the relative importance factors in linear constraints for the minimization.

The acceptable ranges may be provided by the user or automatically. In particular, the ranges may be based on the results of previous optimization steps (related to single objectives). The relative important factors may be set to equal values, e. g. 1 for all the pairs of objectives, or they may be provided by the user or automatically.

In particular, the optimization of the compromise may include the following substeps:
  a) determination of the best possible values of properties relating to two or more optimization objectives of interest, using the method as described above;

b) retrieving from the obtained results the maximum and minimum values for each of these properties or use the information obtained in the previous optimizations to select individual boundaries for the properties relating to the optimization objectives;

c) choose the relative importance between the properties as a factor F (for equal important properties F=1); and d) minimization of one of the properties using the relative importance factors F in a linear constraint or a plurality of linear constraints.

As an alternative to the optimization of the compromise, inequality constraints may be used in the optimization to avoid that optimizing one specific property forces another property in an unacceptable range. However, this does not allow for precisely setting the relative importance of the properties.

Preferably, the method comprises the step of automatically determining an optimum solvent composition for the determined sunscreen composition. The choice of solvents is very relevant for various aspects of the final formulation, including costs and skin feel thereof, cf. e.g. B. Herzog, J. Giesinger, M. Schnyder: "Solubility of UV Absorbers for Sunscreens is Essential for the Creation of Light Feel Formulations", SOFW Journal, 139, 7-2013, 7-14. Accordingly, if the solvent composition is optimized, the properties of the final formulation may be improved.

Advantageously, the optimum solvent composition is determined from a minimization of extra solvents under a constraint that all filter substances of a respective sunscreen composition are dissolved.

For the determination of the optimum solvent composition, a number of solvents (e. g. 4-6 substances) are predetermined.

For the minimization, a numerical optimization may be employed, using a suitable algorithm, such as a Sequential Least Squares Programming (SLSQP) or a Simplex algorithm.

Alternatively, a combinatorial approach is used for the determination of the optimum solvent composition.

If the actual solvent composition is relevant for the optimization objective of the optimization of the sunscreen composition (which is usually the case) the determination of the optimum solvent composition is preferably integrated into the superordinate determination of the sunscreen composition. This allows for finding the overall optimum including the choice of the filter as well as of the solvent composition.

An inventive computer program product comprises instructions which, when executed by a computer, cause the computer to carry out the steps of the inventive method as described above.

In an inventive method of preparing a sunscreen composition the composition is determined as a composition of UV filter substances according to the inventive method as described above. Successively, the sunscreen composition is obtained by combining the UV filter substances.

Other advantageous embodiments and combinations of features come out from the detailed description below and the entirety of the claims.

BRIEF DESCRIPTION OF THE DRAWINGS

The drawings used to explain the embodiments show.

In the figures, the same components are given the same reference symbols.

PREFERRED EMBODIMENTS

Figure 1:
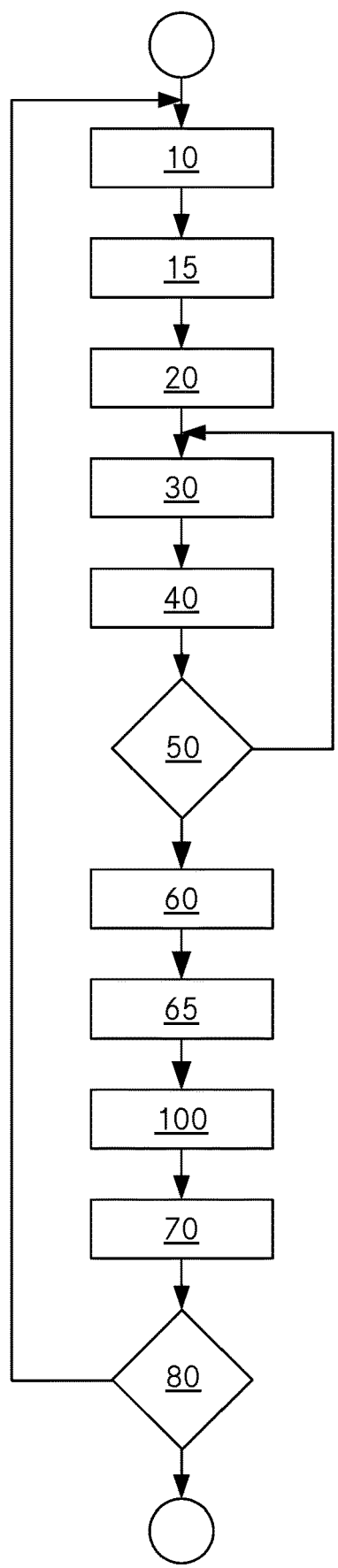
FIG. 1 a flow chart schematically illustrating a method for determining a sunscreen composition comprising a plurality of UV filter substances.

The FIG. 1 is a flow chart schematically illustrating a method for determining a sunscreen composition comprising a plurality of UV filter substances. The method is computer-based, executed by running a dedicated software running on a local computer (e. g. personal computer) or on a server connected to a local user terminal. A user interacts with the local computer or terminal in an interactive fashion. The software may comprise several modules that run on different processors, wherein the processors may be located in the same place or remote from each other. In particular, a local user client (including a web browser or a dedicated client application) may interact with a server software and/or more computationally intensive tasks such as numerical optimization or sunscreen performance simulation may be executed by dedicated processors (e. g. GPUs) or servers.

Basically, it is the goal of the described embodiment of the inventive method, applied by the user, to find a sunscreen composition, including a solvent composition, that meets a sunscreen performance target as well as possibly other constraints and that is optimal with respect to one or several optimization objectives.

First of all, the user selects an actual set of filter substances to be considered (step 10). For this purpose a list including a basic set of filter substances is displayed and the user selects the desired substances. Furthermore, the user has the opportunity to provide minimum and maximum amounts for at least some of the filter substances (step 15). This is not mandatory, the user may leave the corresponding input fields empty, which signifies that the amount of the respective filter substance may be as low as 0 (no minimum indicated) or as high as 100% (no maximum indicated) or the maximal amount is automatically retrieved from the regulatory limits in a user specified region or in an automatically detected region, e.g. by language and/or location settings on the computer of the user or by positioning data, if available.

Next, the user provides information on the required sunscreen performance target (step 20). For that purpose, the user selects one of the following available properties relating to the sunscreen performance:

in vivo or in vitro Sun Protection Factor SPF (e. g. dedicated SPF or protection category);

in vivo or in vitro UVA Protection Factor UVAPF (e. g. dedicated IPD or JCIA);

critical wavelength;

ratio of UVA to UVB protection (e. g. based on the Boots Star® rating);

blue light protection.

Furthermore, the user provides the target value for the selected property, e. g. in vivo SPF≥30.

Next, the user has the opportunity to select further constraints for at least one characteristic of the combination to be determined (step 30). These constraints may relate to the following properties:

a value or range for the total amount of filter substances;

a value or range for the amount of a certain filter substance;

a maximum value for the costs of the composition of filter substances;

a value or range for the weighting of the composition of filter substances;

a value or range for an eco-friendliness parameter of the composition;

a value or range or maximum amount of extra solvent;

a maximum oil load.

The constraints are presented on the screen and the user selects the desired additional constraints. Depending on the constraint, input fields for set values, minimum and/or maximum values are displayed. The user is free to select no further constraint, one further constraint or a plurality of further constraints.

Next, the user selects one or several optimization objectives (step 40) from the following plurality of optimization objectives:

cost efficiency;
weighting;
filtering efficiency;
eco-friendliness;
amount of extra solvent;
minimal oil load;
homogenous protection;
sun protection factor and/or UVA protection factor;
blue light protection;
similarity to a provided composition of filter substances.

The weighting of a filter is a number, which may represent the price of the filter, a score how eco-friendly the filter is, a score how easy it is to formulate the filter, a score for the impact of the filter on the sensory to the sunscreen, etc. The weighting of a filter combination is the sum of the weightings of individual filters multiplied with their corresponding percentages in this combination and may therefore represent e.g. the total costs of the filter combination, total sensory impact, etc.

The minimal oil load is the sum of all filters in the oil phase plus the extra solvent, which may be required to dissolve solid filters. It is a good measure of how much freedom a formulator has with a particular filter combination. This is due to the fact that usually a certain total oil load of the final product shall not be exceeded, because very high oil loads lead to an unfavourable heavy feeling of the product. If the minimum oil load due to the filter substances is already quite high the freedom of adding further oil-based substances is very limited.

After the selection of the objective(s) it is checked whether the selected objective(s) are compatible with the further constraints provided before (decision 50). If this is not the case, e. g. because the property that shall be optimized is subject of a constraint, a warning message is displayed. The user then has the opportunity to release the corresponding constraint or to select another objective.

Finally, the user selects an actual set of solvent substances to be considered (step 60). For this purpose a list including a basic set of solvent substances is displayed and the user selects the desired substances. Furthermore, the user has the opportunity to provide minimum and maximum amounts for at least some of the solvent substances (step 65). This is not mandatory, the user may leave the corresponding input fields empty, which signifies that the amount of the respective solvent substance may be as low as 0 (no minimum indicated) or as high as 100% (no maximum indicated).

Once the user has provided all information, an optimum sunscreen composition is automatically determined as a composition of substances from the selected actual set of filter substances as well as an optimized composition of solvents adapted for the respective composition of filter substances (step 100). The composition achieves the performance target and meets all possible further constraints. It is optimized with respect to the selected objective(s).

The output to the user (step 70) includes the filter substances and their corresponding amounts as well as the solvents and their corresponding amounts. It further includes numerous properties characterizing the corresponding composition, including the achieved performance, the UVA/SPF ratio, the total amount of filter substances, the efficiency (see below), the weighting, the minimal oil load and the costs.

As described in more detail below, the optimization includes the calculation of the sunscreen performance of various candidate compositions using an available performance simulation tool.

Based on the results, the user may decide whether the found composition is the desired one or whether the input parameters, e. g. the choice of filter and/or solvent substances, the corresponding ranges for their amounts or the further constraints, shall be adjusted for a next optimization step (decision 80). Alternatively or in addition, the optimization may be done for another objective or a combination of objectives, wherein the input parameters may be adjusted based on the results of the previous optimization step(s).

In one preferred embodiment, the optimum sunscreen composition is automatically determined using a numerical optimization of an objective function related to the selected optimization objective, the variables of the objective function including proportions of the filter substances of the sunscreen composition to be determined.

In the described example, the optimization is performed using the 'trust-constr' method available in the open-source library SciPy, release 1.4 of 19 Dec. 2019 for the Python programming language (cf. SciPy.org). The method is based on the EQSQP algorithm (Lalee, Marucha, Jorge Nocedal, and Todd Plantega: "On the implementation of an algorithm for large-scale equality constrained optimization", SIAM Journal on Optimization 8.3: 682-706, 1998).

The objective function depends on the optimization objective. Several examples are given in the following:

One possible objective is finding the most efficient UV filter combination. This is the combination which achieves the desired performance targets with the minimal total amount of UV filters. In the following formula the number of individual filters is given by k and the concentration of filter i is given as $x_i$.

The objective is $$\min_{x \in \mathbb{R}^k} \sum_{i=1}^{k} x_i$$

subject to e. g.

$SPF_{simulated}(\vec{x}) \geq SPF_{desired}$, i. e. the target sun protection factor is achieved, the ratio between the UVA protection factor and the SPF meets $$\frac{UVAPF_{simulated}(\vec{x})}{SPF_{simulated}(\vec{x})} \geq 0.33,$$

the critical wavelength $\lambda_{crit,simulated} \geq 370$ nm and the (simulated) amount of required extra solvent is less or equal than 10%.

Furthermore, the amounts of the UV filters are restricted to the indicated minimum and maximum values:

$$\overrightarrow{\text{lower boundaries}} \leq \vec{x} \leq \overrightarrow{\text{upper boundaries}}.$$

Another objective relates to the weighting of the UV filter combination. The weighting of a filter is a number, which may represent the price of the filter, a score how eco-friendly the filter is, a score how easy it is to formulate the filter, a score for the impact of the filter on the sensory of the sunscreen, etc. and is given in the following formulas as $\vec{w}$.

The weighting of a filter combination is the sum of the weightings of individual filters multiplied with their corresponding percentages (given in the following formula as $\vec{x}$) in this combination (dot product) and may therefore represent e.g. the total costs of the filter combination, total sensory impact, etc.

The objective is $$\min_{x \in \mathbb{R}^k} \vec{x} \cdot \vec{w}$$

subject to the performance and property constraints as indicated above, in the previous example.

Another objective relates to the minimal oil load of the composition. This is the sum of the concentrations of all m filters in the oil phase plus extra solvent or solvent mixtures, which may be required to completely dissolve all solid filters. It is a good measure how much freedom a formulator has with a particular filter combination.

The objective is $$\min_{x \in \mathbb{R}^m} \sum_{i=1}^{m} x_i^{oil\ phase} + \text{minimal extra solvents}_{simulated}(\vec{x})$$

again subject to the performance and property constraints as indicated above, where minimal extra solvents$_{simulated}(\vec{x})$ denotes the total amount of extra solvents of an optimal (minimal) solvent mixture. The composition of this mixture may be determined with various optimization algorithms such as e.g. a Sequential Least SQuares Programming (SLSQP) algorithm (also available in the SciPy library, method 'SLSQP') or a Simplex algorithm (method 'simplex' in the SciPy library).

Assume that a (candidate) filter composition 2 includes n solid UV filter substances and m liquid UV filter substances. The situation regarding the dissolution of the solid UV filter substances may be formulated as follows:

$$\begin{bmatrix} c_1 \\ c_2 \\ \vdots \\ c_n \end{bmatrix} - \begin{bmatrix} s_1^1 & s_2^1 & \dots & s_n^1 \\ s_1^2 & s_2^2 & \dots & s_n^2 \\ \vdots & \vdots & \vdots & \vdots \\ s_1^m & s_2^m & \dots & s_n^m \end{bmatrix} \cdot \begin{bmatrix} l_1 \\ l_2 \\ \vdots \\ l_m \end{bmatrix} = \begin{bmatrix} r_1 \\ r_2 \\ \vdots \\ r_n \end{bmatrix} \text{ or } \vec{c} - S \cdot \vec{l} = \vec{r},$$

where $\vec{c}$ is a vector containing the concentrations of the n solid UV filter substances and $\vec{l}$ is a vector containing the concentrations of the m liquid UV filters. The elements of the matrix S are defined as follows:

$$s_i^j = \frac{\text{solubility of filter}_i \text{ in filter}_j}{100 - \text{solubility of filter}_i \text{ in filter}_j}$$

Accordingly, the resulting vector $\vec{r}$ reflects the concentrations of the n solid UV filters that are not dissolved by the m liquid UV filters.

The condition to completely dissolve the solid UV filters may now be stated as follows:

$$\begin{bmatrix} a_1^1 & a_2^1 & \dots & a_n^1 \\ a_1^2 & a_2^2 & \dots & a_n^2 \\ \vdots & \vdots & \vdots & \vdots \\ a_1^m & a_2^m & \dots & a_n^m \end{bmatrix} \cdot \begin{bmatrix} y_1 \\ y_2 \\ \vdots \\ y_m \end{bmatrix} = \begin{bmatrix} b_1 \\ b_2 \\ \vdots \\ b_n \end{bmatrix} \text{ or}$$

$$A \cdot \vec{y} = \vec{b} \text{ with } \vec{y} \geq 0 \text{ and } b = \begin{cases} 0 & \text{if } r \leq 0 \\ r & \text{otherwise} \end{cases},$$

where $$a_i^j = \frac{\text{solubility of filter}_i \text{ in solvent}_j}{100 - \text{solubility of filter}_i \text{ in solvent}_j}$$

and where the vector $\vec{y}$ contains the concentrations of (additional) solvents. The solubilities may be obtained e. g. using a method as described in B. Herzog, J. Giesinger, M. Schnyder: "Solubility of UV Absorbers for Sunscreens is Essential for the Creation of Light Feel Formulations", SOFW Journal, 139, 7-2013, 7-14.

The combination of minimal extra solvents $\vec{y}*$ is now obtained by solving $$A \cdot \vec{y} = \vec{b}$$

using the Simplex method (or any other suitable method).

Another objective relates to the similarity of the composition to a (user) provided composition. This allows for adjusting known composition in such a way that performance targets are achieved and constraints are met. The objective may be stated as follows:

$$\min_{x \in \mathbb{R}^k} \sqrt{\sum_{i=1}^{k} (x_i - u_i)^2},$$

where $u_i$ relates to the amounts of filters of the user provided composition. Accordingly, it is the Euclidean distance of the composition to be determined from the suggestion provided that shall be minimized.

The optimization will result in an adjustment that preserves the principle idea of the user as close as possible and that quickly adjusts the filter concentrations to meet the desired performance target and the constraints.

Up to here, it has been assumed that the user has chosen a single optimization objective. However, often optimizing one specific property such as efficiency may force another property such as costs in an unacceptable range. A possible solution to this issue is to set a corresponding inequality constraint for this property.

A much more versatile method is to search for an optimal compromise of two or more properties according to the procedure described in the following.

First the properties of interest are identified. The sunscreen compositions are successively optimized with respect to each of these properties as described above. This yields maximum and minimum values for each of the properties of interest.

Next, individual property boundaries $p^{min}$, $p^{max}$ are set. They may be automatically set to the minimum and maximum values obtained from the optimizations or set by the user, taking into account the minimum and maximum values.

In a further step, the relative importance between the properties is chosen as a factor F. For equally important properties F=1

Finally, one of the properties $p_i$ of interest is minimized using the relative importance factor(s) in linear constraint(s) as follows:

$$\text{general: } \frac{1}{D_i} * f_i(\vec{x}) - \frac{F}{D_j} * f_j(\vec{x}) = \frac{p_i^{min}}{D_i} - \frac{F * p_j^{min}}{D_j},$$

$$\text{weighting: } \left(\frac{1}{D_i} * \vec{w}_i - \frac{F}{D_j} * \vec{w}_j\right) \cdot \vec{x} = \frac{p_i^{min}}{D_i} - \frac{F * p_j^{min}}{D_j},$$

where $\vec{x}$ contains the concentrations of the UV filters, $\vec{w}_n$ the weighting for the property $p_n$ and $D_n = p_n^{max} - p_n^{min}$, where in the general case $f_n(\vec{x}) = p_n \cdot \vec{x}$ and for weighting $f_n(\vec{x}) = \vec{w}_n \cdot \vec{x} = p_n \cdot \vec{x}$.

The usual performance and property constraints as described above apply as well.

Figure 2:
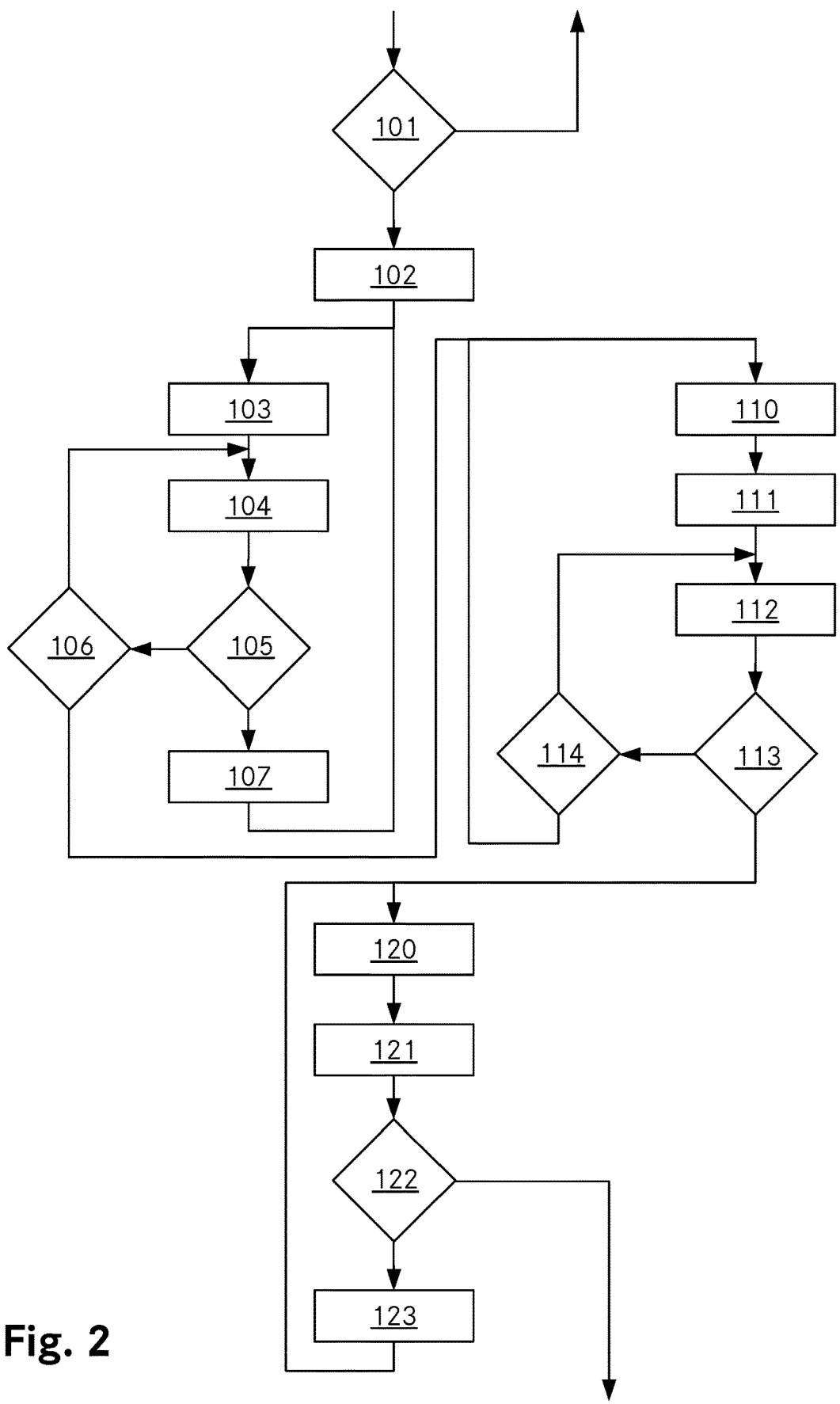
FIG. 2 a flow chart schematically illustrating the combinatorial method for finding an optimized sunscreen composition.

Instead of the numerical optimization, in a further embodiment the optimum sunscreen composition is automatically determined using a combinatorial approach. The FIG. 2 is a flow chart schematically illustrating this combinatorial method for finding an optimized sunscreen composition (step 100 in the process of FIG. 1). In this context, a plurality of candidate compositions are automatically defined, and the sunscreen performance of at least some of the plurality of candidate compositions is determined using the performance simulation tool.

Such an approach is feasible, if various measures are applied to reduce the number of calculations, which are:

1) Reducing the number of UV filters by a preselection of a maximum of 6 filters. Before continuing, it is checked whether the number of filters exceeds 6 (decision 101). If this is the case the user is asked to reduce the number of selected filters or to switch to numerical optimization.
2) Choosing an increment for the automatic definition of compositions to 0.5-1.0 wt %, preferably to 0.5 wt %.
3) Reducing the search space by:
   3a) Searching for the lowest total filter amount capable to achieve the targeted performance by:
      a. conservatively estimating the total amount of filters necessary to achieve the performance target (step 102), e.g. SPF/2 wt %, and calculate only combinations with a corresponding total amount of filters. (For SPF=30, with 6 filters, an increment of 0.5 wt % and a maximal use level of 5 wt % per filter and restricting to a total concentration of 15 wt % (SPF 30/2) 312620 calculations are required);
      b. enumerating the corresponding filter combinations in a way that combinations with most of the most efficient filters are tested first (step 103);
      c. next, it is checked whether the target performance can be met with the present total amount of filters, for that purpose:
         the performance of a candidate composition is determined using the performance simulation tool (step 104);
         it is checked whether the determined performance meets the performance target (decision 105); if this is not the case, it is checked whether further candidate compositions are remaining (decision 106), if this is the case, the next candidate composition (according to the enumeration) is checked
      d. if the determined performance of one of the candidate compositions meets the target, the calculation is stopped (this happens typically within less than 1000 calculations), the amount of filters is reduced by a fixed number, e. g. 1 wt % (step 107) and the resulting candidate compositions are enumerated and checked as described before (steps 103-106); this is repeated until the target is not achievable any more, i. e. none of the compositions meets the target (no further candidate compositions in decision 106) (backward search);
      e. next, the total amount of filters is increased by an increment (e.g. 0.5 wt %) (step 110) the resulting candidate compositions are enumerated (step 111) and it is checked whether the target performance can be met with the present total amount of filters, for that purpose:
         the performance of a candidate composition is determined using the performance simulation tool (step 112);
         it is checked whether the determined performance meets the performance target (decision 113); if this is not the case, it is checked whether further candidate compositions are remaining (decision 114), if this is the case, the next candidate composition (according to the enumeration) is checked
      f. if the determined performance of one of the candidate compositions meets the target, the calculation is stopped (this happens typically within less than 1000 calculations); if none of the candidate compositions meets the target, the amount of filters is increased once more by a fixed number, e. g. 0.5 wt % (step 110) and the resulting candidate compositions are enumerated and checked as described before (steps 111-114); this is repeated until the target is achieved, i. e. at least one of the compositions meets the target (no further candidate compositions in decision 114) (forward search);
   This will give the lowest total filter amount (most efficient filter combination(s)) capable to achieve the target performance.
   3b) Start from the lowest feasible total filter amount and search optimal solutions by increasing the total amount by one increment for each search e.g. 0.5 wt %. This is achieved by
   reducing the search space as described above (step 120);
   calculating the relevant properties for the remaining candidate compositions having a fixed total filter amount, starting with the determined lowest total filter amount (step 121);
   checking whether the property relating to the selected optimization objective has improved compared to the previous run (decision 122); if this is the case, the total filter amount is increased by the mentioned increment (step 123) and the determination is repeated with the increased value (steps 120-122);

if there is no further improvement (decision 122) the best composition (or a list of best compositions) with respect to the selected optimization objective is returned for further processing.

Many properties such as costs, extra solvent and minimal oil load normally decrease with higher total filter amount until the optimum is reached. Thus, it is often possible to continue this forward search as long as the property value decreases and stop as soon as it starts to increase again with increased total filter amount. Otherwise the search has to be continued until the maximal total amount of UV filters is reached.

Linear objective functions (e.g. most efficient or cost-efficient UV filter combinations) can be evaluated by simple dot products and therefore very efficiently calculated by matrix operations on regular computers. In these cases, all combinations can be efficiently evaluated at once followed by sequential block wise performance predictions. The current optimum within previous blocks (e.g. lowest cost) can be used to skip all performance predictions from residual combinations with worse values compared to this optimum. Typically, this reduction of the search space (step 120) allows to find the optimum with less than 3000 calculations for a given total amount of filters.

Using the combinatorial approach allows for displaying not only a single optimized composition but a list of best candidate compositions, e. g. 10 or 20 compositions, together with their properties. This provides additional valuable information to the user. In particular, the user is enabled to identify whether the best solutions feature a very similar composition of filter substances or whether they relate to substantially different compositions. In the latter case, based on his or her knowledge, the user might decide to choose only the second or third best composition or to continue with the next optimization step based on the second or third best composition because it appears to be a better starting point for further improvement.

It may be possible for the user to choose between the numerical optimization and the combinatorial approach for every iteration step. As an example, once a promising composition has been found using the combinatorial approach it may be further improved by applying a numerical optimization step, starting from the identified candidate composition. This is because the numerical approach allows for more precise amounts for the constituents of the composition than the combinatorial approach where the possible values are discrete. Vice versa it is possible to double check whether the numerical approach has indeed found the true global minimum in the optimization using the combinatorial approach.

Switching to the combinatorial approach may also be useful in order to obtain a ranked result list.

In all embodiments of the present invention, preferably the UV-filter substances are to be selected from the group consisting of octyl methoxycinnamate (PARSOL® MCX), isoamyl methoxycinnamate (Neo Heliopan® E 1000), homosalate (3,3,5 trimethylcyclohexyl 2-hydroxybenzoate, PARSOL® HMS) ethylhexyl salicylate (also known as ethylhexyl salicylate, 2 ethylhexyl 2-hydroxybenzoate, PARSOL® EHS), octocrylene (2 ethylhexyl 2-cyano-3,3-diphenylacrylate, PARSOL® 340), polysilicone 15 (PARSOL® SLX), diethylhexyl 2,6-naphthalate (Corapan® TQ), syringylidene malonates such as e.g. diethylhexyl syringylidene malonate (Oxynex® ST liquid), benzotriazolyl dodecyl p-cresol (Tinoguard® TL) as well as benzophenone-3 and drometrizole trisiloxane, bis-ethyl¬hexyloxyphenol methoxyphenyl triazine (PARSOL® SHIELD), butyl methoxydibenzoyl methane (PARSOL® 1789), methy¬lene bis-benzotriazolyl tetramethylbutylphenol (PARSOL® MAX), diethylamino hydroxybenzoyl hexyl benzoate (UVINUL® A PLUS), ethylhexyl triazone (UVINUL® T150), diethylhexyl butamido triazone (Uvasorb® HEB), Tris-Biphenyl Triazine (Uvinul® A2B) 4-methyl¬benzylidene camphor (PARSOL® 5000) and 1,4-di(benzoxazol-2'-yl)benzene bis-ethylhexyloxyphenol methoxyphenyl triazine, Phenylbenzimidazole Sulfonic Acid (PARSOL® HS) and Disodium Phenyl Dibenzimidazole Tetrasulfonate (Neoheliopan® AP), microfine (preferably coated) titanium dioxide (e.g. PARSOL® TX) and Zinc Oxid (e.g. PARSOL® ZX).

The methods described above have been used to calculate optimized compositions of UV filter substances, subject to different constraints and optimization objectives:

Example 1

In a first example, the objective was to find the most efficient UV filter combination, i. e. achieving the desired performance target with minimal total amount of UV filters.

The following filter substances have been chosen with the indicated boundaries and weightings:

| INCI Name | Boundaries | Weighting |
|---|---|---|
| Homomenthyl Salicylate | ≤10 wt % | 20 |
| Butyl Methoxydibenzoylmethane | ≤5 wt % | 50 |
| Bis-Ethy lhexyloxyphenol Methoxyphenyl Triazine | ≤4 wt % | 150 |
| Octocrylene | ≤10 wt % | 25 |
| Diethy lhexyl Butamido Triazone | ≤5 wt % | 100 |
| Phenylbenzimidazol Sulfonic Acid | ≤2 wt % | 50 |

The performance constraints were SPF≥30 and the ratio UVAPF/SPF≥0.33. No property constraints were applied.

An optimized composition has been determined using the methods described above, the optimized combinatorial approach (with an increment of 0.5 wt %, up to 5.0 wt %, resulting in 1.28 million possible combinations) and the numerical optimization. The results were as follows:

| | optimal wt % | |
|---|---|---|
| INCI Name | combinatorial | numerical |
| Homomenthyl Salicylate | 0.0 | 0.00 |
| Butyl Methoxydibenzoylmethane | 1.5 | 1.04 |
| Bis-Ethy lhexyloxyphenol Methoxyphenyl Triazine | 2.5 | 3.03 |
| Octocrylene | 0.0 | 0.00 |
| Diethylhexyl Butamido Triazone | 3.0 | 2.85 |
| Phenylbenzimidazol Sulfonic Acid | 2.0 | 2.00 | with the following properties:

| property | combinatorial | numerical. |
|---|---|---|
| SPF | 30.0 | 30.0 |
| UVA/SPF ratio | 0.35 | 0.33 |
| Total amount, % | 9 | 8.94 |
| Efficiency | 3.33 | 3.36 |
| Weighting | 8.5 | 8.41 |
| Minimal Oil Load, % | 25.3 | 29.1 |
| CPU (2.9 GHZ) time, s | 5 | <1 |

Example 2

In a second example, the objective was to find the most weighting-efficient UV filter combination.

The filter substances, their boundaries and weightings as well as the constraints have been the same as in Example 1. The results of the two methods were as follows:

|  | optimal wt % | |
|---|---|---|
| INCI Name | combinatorial | numerical |
| Homomenthyl Salicylate | 0.0 | 0.00 |
| Butyl Methoxydibenzoylmethane | 2.5 | 2.61 |
| Bis-Ethylhexyloxyphenol Methoxyphenyl Triazine | 0.0 | 0.00 |
| Octocrylene | 9.0 | 10.00 |
| Diethylhexyl Butamido Triazone | 1.0 | 0.57 |
| Phenylbenzimidazol Sulfonic Acid | 2.0 | 2.00 | with the following properties:

| property | combinatorial | numerical |
|---|---|---|
| SPF | 30.2 | 30.0 |
| UVA/SPF ratio | 0.41 | 0.44 |
| Total amount, % | 14.5 | 15.2 |
| Efficiency | 2.07 | 1.97 |
| Weighting | 5.5 | 4.89 |
| Minimal Oil Load, % | 13.0 | 13.2 |
| CPU (2.9 GHz) time, s | 12 | 0.9 |

Example 3

In a third example, the objective was to find the UV filter combination with the minimal oil load.

The filter substances, their boundaries and weightings have been the same as in Examples 1 and 2. The performance constraints were SPF≥30 and the ratio UVAPF/SPF≥0.33. The property constraints were a maximal weighting of 6.5 and a maximum total amount of filters of 17%.

The results of the two methods were as follows:

|  | optimal wt % | |
|---|---|---|
| INCI Name | combinatorial | numerical |
| Homomenthyl Salicylate | 0.0 | 0.81 |
| Butyl Methoxydibenzoylmethane | 2.0 | 1.67 |
| Bis-Ethylhexyloxyphenol Methoxyphenyl Triazine | 0.5 | 0.59 |
| Octocrylene | 9.0 | 5.76 |
| Diethylhexyl Butamido Triazone | 1.0 | 2.00 |
| Phenylbenzimidazol Sulfonic Acid | 2.0 | 2.00 | with the following properties:

| property | comb. | num. opt. |
|---|---|---|
| SPF | 30.7 | 30.0 |
| UVA/SPF ratio | 0.38 | 0.33 |
| Total amount, % | 14.5 | 12.8 |
| Efficiency | 2.07 | 2.34 |
| Weighting | 6.0 | 6.3 |
| Minimal Oil Load, % | 12.5 | 10.8 |
| CPU (2.9 GHz) time, s | 7 | 20 |

Example 4

In a fourth example, the objective was to find the most weighting-efficient UV filter combination.

In contrast to the Examples 1-3, 10 instead of 6 filter substances have been selected, with the indicated boundaries and weightings:

| INCI Name | Boundaries | Weighting |
|---|---|---|
| Homomenthyl Salicylate | ≤5 wt % | 20 |
| Butyl Methoxydibenzoylmethane | ≤5 wt % | 50 |
| Bis-Ethylhexyloxyphenol Methoxyphenyl Triazine | ≤4 wt % | 150 |
| 4-Methylbenzylidene Camphor | ≤4 wt % | 75 |
| Ethylhexyl Salicylate | ≤5 wt % | 20 |
| Octocrylene | ≤10 wt % | 25 |
| Diethylamino Hydroxybenzoyl Hexyl Benzoate | ≤10 wt % | 75 |
| Ethylhexyl Triazone | ≤3 wt % | 100 |
| Titanium Dioxide | ≤20 wt % | 75 |
| Methylene Bis-Benzotriazolyl Tetramethylbutylphenol, active | ≤8 wt % | 150 |

The performance constraints were SPF≥50 and the ratio UVAPF/SPF≥0.33. No property constraints were applied.

An optimization using the combinatorial approach was not feasible because even with an increment of 0.5 wt % a number of 98 billion possible combinations would have been required to be checked. This is not feasible on a regular computer.

The results of the numerical optimization were as follows:

| INCI Name | optimal wt % |
|---|---|
| Homomenthyl Salicylate | 5.00 |
| Butyl Methoxydibenzoylmethane | 5.00 |
| Bis-Ethylhexyloxyphenol Methoxyphenyl Triazine | 0.00 |
| 4-Methylbenzylidene Camphor | 0.26 |
| Ethylhexyl Salicylate | 5.00 |
| Octocrylene | 10.00 |
| Diethylamino Hydroxybenzoyl Hexyl Benzoate | 0.00 |
| Ethylhexyl Triazone | 3.00 |
| Titanium Dioxide | 2.27 |
| Methylene Bis-Benzotriazolyl Tetramethylbutylphenol, active | 1.06 | with the following properties:

| SPF | 50.0 |
|---|---|
| UVA/SPF ratio | 0.33 |
| Total amount, % | 31.6 |
| Efficiency | 1.58 |
| Weighting | 13.5 |
| Minimal Oil Load, % | 40.2 |
| CPU (2.9 GHz) time, s | 1 |

Example 5

In a fifth example, the objective was to find the most efficient UV filter combination.

The filter substances, their boundaries and weightings as well as the constraints have been the same as in Example 4.

Again, the combinatorial method was not feasible due to the same reasons. The results of the numerical optimization was as follows:

| INCI Name | optimal wt % |
|---|---|
| Homomenthyl Salicylate | 0.00 |
| Butyl Methoxydibenzoylmethane | 0.00 |
| Bis-Ethylhexyloxyphenol Methoxyphenyl Triazine | 4.00 |
| 4-Methylbenzylidene Camphor | 0.76 |
| Ethylhexyl Salicylate | 0.00 |
| Octocrylene | 0.00 |
| Diethylamino Hydroxybenzoyl Hexyl Benzoate | 0.00 |
| Ethylhexyl Triazone | 3.00 |
| Titanium Dioxide | 0.00 |
| Methylene Bis-Benzotriazolyl Tetramethylbutylphenol, active | 8.00 | with the following properties:

| | |
|---|---|
| SPF | 50.0 |
| UVA/SPF ratio | 0.43 |
| Total amount, % | 15.76 |
| Efficiency | 3.17 |
| Weighting | 21.6 |
| Minimal Oil Load, % | 39.2 |
| CPU (2.9 GHz) time, s | 1 |

Example 6

In a sixth example, the objective was to find a compromise for the weighting and the efficiency (with equal weight of the two objectives).

The filter substances, their boundaries and weightings as well as the constraints have been the same as in Examples 4 and 5.

Again, the combinatorial method was not feasible due to the reasons mentioned. The results of the numerical optimization was as follows:

| INCI Name | optimal wt % |
|---|---|
| Homomenthyl Salicylate | 0.00 |
| Butyl Methoxydibenzoylmethane | 4.10 |
| Bis-Ethylhexyloxyphenol Methoxyphenyl Triazine | 0.20 |
| 4-Methylbenzylidene Camphor | 3.52 |
| Ethylhexyl Salicylate | 1.73 |
| Octocrylene | 5.20 |
| Diethylamino Hydroxybenzoyl Hexyl Benzoate | 0.00 |
| Ethylhexyl Triazone | 3.00 |
| Titanium Dioxide | 0.00 |
| Methylene Bis-Benzotriazolyl Tetramethylbutylphenol, active | 4.55 | with the following properties:

| | |
|---|---|
| SPF | 50.0 |
| UVA/SPF ratio | 0.39 |
| Total amount, % | 20.57 |
| Efficiency | 2.43 |
| Weighting | 16.11 |
| Minimal Oil Load, % | 30.6 |
| CPU (2.9 GHz) time, s | 1 |

The comparison of the properties with Examples 4 and 5, where the composition has been optimized for the single objectives, leads to the following:

| property | Ex. 4 | Ex. 5 | Ex. 6 |
|---|---|---|---|
| SPF | 50.1 | 50.2 | 50.0 |
| UVA/SPF ratio | 0.33 | 0.48 | 0.39 |
| Total amount, % | 31.7 | 15.77 | 20.57 |
| Efficiency | 1.58 | 3.18 | 2.43 |
| Weighting | 13.6 | 22.2 | 16.11 |
| Minimal Oil Load, % | 40.1 | 38.5 | 30.6 |
| CPU (2.9 GHz) time, s | 1 | 1 | 1 |

As can be seen from the results, the compromise is established as follows:

$$\frac{w - w_{min}}{w_{max} - w_{min}} = \frac{16.11 - 13.6}{22.2 - 13.6} = 0.29 \approx 0.30 = \frac{1.58}{2.43} \cdot \frac{3.18 - 2.43}{3.18 - 1.58} = \frac{E_{min}}{E} \cdot \frac{E_{max} - E}{E_{max} - E_{min}},$$

where it has been taken into account that the value for the weighting is minimized and that the value for the efficiency is maximized. Accordingly, the deviation of the resulting efficiency from the optimum value as well as the deviation of the resulting weighting from the optimum value are about the same.

Example 7

In a seventh example, the objective was to find a compromise for the weighting and the efficiency, similar to the sixth example, but now with the aim of a 100/50 weighting/efficiency compromise (F=2).

The filter substances and their boundaries have been the same as in Examples 4-6. In addition to the unchanged constraints on the SPF and the UVAPF/SPF ratio the following property constraints have been imposed:

maximum weighting $w_{max} \leq 18.0$;
maximum total amount of filters $a_{max} \leq 25\%$ (i. e. $E_{min} \geq 2.0$).

Again, the combinatorial method was not feasible due to the reasons mentioned. The results of the numerical optimization was as follows:

| INCI Name | optimal wt % |
|---|---|
| Homomenthyl Salicylate | 0.00 |
| Butyl Methoxydibenzoylmethane | 4.26 |
| Bis-Ethylhexyloxyphenol Methoxyphenyl Triazine | 0.00 |
| 4-Methylbenzylidene Camphor | 2.41 |
| Ethylhexyl Salicylate | 0.00 |
| Octocrylene | 8.38 |
| Diethylamino Hydroxybenzoyl Hexyl Benzoate | 0.00 |
| Ethylhexyl Triazone | 3.00 |
| Titanium Dioxide | 0.00 |
| Methylene Bis-Benzotriazolyl Tetramethylbutylphenol, active | 4.04 | with the following properties:

| | |
|---|---|
| SPF | 50.0 |
| UVA/SPF ratio | 0.39 |
| Total amount, % | 22.09 |
| Efficiency | 2.26 |
| Weighting | 15.09 |

-continued

| | |
|---|---|
| Minimal Oil Load, % | 32.0 |
| CPU (2.9 GHz) time, s | 1 |

Again, the check of the results shows that the compromise reflects the desired relative weight of the two objectives (F=2):

$$\frac{w - w_{min}}{w_{max} - w_{min}} = \frac{15.09 - 13.6}{18.0 - 13.6} =$$

$$0.34 \approx \frac{1}{2} 0.69 = \frac{1}{2} \frac{2.0}{2.26} \frac{3.18 - 2.26}{3.18 - 2.00} = \frac{1}{F} \cdot \frac{E_{min}}{E} \cdot \frac{E_{max} - E}{E_{max} - E_{min}}.$$

The invention is not restricted to the embodiments described above. In particular, the number and succession of method steps may be different and the user may be provided more or less options to interact with the process or to enter information. Some of the required information may be automatically provided, e. g. retrieved from a database. In contrast to the described embodiment, even the iterative process may be computer assisted or computer guided, i. e. successive optimizations with different input parameters and/or objectives may suggested to the user or automatically performed.

For the numerical optimization other algorithms may be employed. One readily available method involves a Sequential Least SQuares Programming (SLSQP) algorithm, available e. g. in the SciPy library mentioned above. It may also be possible to optimize using further methods, such as line search methods or penalty/augmented Lagrangian algorithms.

In summary, it is to be noted that the invention creates a method that allows for the efficient determination of optimum sunscreen compositions.

The invention claimed is:

1. A method of preparing a sunscreen composition, wherein the sunscreen composition is determined as a composition of UV filter substances, the composition of UV filter substances including corresponding amounts of the UV filter substances, with a computer-based method for determining the sunscreen composition comprising a plurality of UV filter substances, comprising the steps of:
a) selecting at least one constraint for at least one characteristic of the composition to be determined, the at least one constraint comprising a sunscreen performance target, the sunscreen performance target being chosen from one of the following:
in vivo or in vitro Sun Protection Factor SPF;
in vivo or in vitro UVA Protection Factor UVAPF;
critical wavelength;
ratio of UVA to UVB protection; and
blue light protection;
b) selecting an optimization objective from a plurality of optimization objectives;
c) automatically determining the sunscreen composition as a composition of filter substances from a set of filter substances, and corresponding amounts of those filter substances, the sunscreen composition meeting the at least one constraint and being optimized with respect to the selected optimization objective, the automatic determination comprising the steps of:
generating a plurality of candidate compositions,
determining a sunscreen performance of the candidate compositions using a performance simulation tool and
comparing the determined sunscreen performance of the candidate compositions with the sunscreen performance target,
wherein the automatic determination of the sunscreen Composition comprises a numerical optimization of an objection function related to the selected optimization objective, the variables of the objective function proportions of the filter substances of the sunscreen composition to be determined,
using a numerical optimization algorithm which evaluates a first and a second derivative of the objective function for its choice of a search direction and step size taken at each iteration,
wherein for the automatic determination of the sunscreen composition, a plurality of candidate compositions are automatically defined and the sunscreen performance of at least some of the plurality of candidate compositions is determined using the performance simulation tool, wherein in a first substep, a lowest total amount of filter substances is determined for a composition that achieves the sunscreen performance target, and wherein in a subsequent second substep, a constraint on a value of the total amount of filter substances of the candidate compositions is gradually increased, starting from the determined lowest total amount, until a stop criterion is met,
wherein successively, the sunscreen composition is obtained by combining the UV filter substances in the corresponding amounts of the UV filter substances.

2. The method as recited in claim 1, wherein a user is requested to select the at least one constraint.

3. The method as recited in claim 2, a sequence including the steps a)-c) being repeated, wherein the user iteratively adjusts the at least one constraint.

4. The method as recited in claim 1, wherein a user is requested to select the optimization objective.

5. The method as recited in claim 4, wherein a sequence including the steps a)-c is repeated, wherein the user iteratively adjusts the optimization objective.

6. The method as recited in claim 1, wherein the user selects an actual set of filter substances to be considered from a basic set of filter substances.

7. The method as recited in claim 6, wherein the user provides a maximum amount of at least some of the selected filter substances.

8. The method as recited in claim 6, wherein the user provides a minimum amount of at least some of the selected filter substances.

9. The method as recited in claim 1, comprising the step of selecting at least one further constraint for at least one characteristic of the composition to be determined.

10. The method as recited in claim 9, the at least one further constraint being a range or a boundary value relating to one of the following properties:
a) total amount of filter substances;
b) amount of one or more distinct filter substances;
c) costs of the composition of filter substances;
d) amount of extra solvent;
e) oil load.

11. The method as recited in claim 1, wherein the plurality of optimization objectives include at least two of the following:
   a) cost efficiency;
   b) filtering efficiency;
   c) amount of extra solvent;
   d) minimal oil load;
   e) most homogenous protection;
   f) highest sun protection factor and/or UVA protection factor;
   g) highest blue light protection; and
   b) similarity to a provided composition of filter substances.

12. The method as recited in claim 1, the numerical optimization comprising an application of a sequential quadratic programming method.

13. The method as recited in claim 12, the numerical optimization comprising an application of an interior-point method.

14. The method as recited in claim 1, wherein the lowest total amount of filter substances is determined by gradually reducing a total amount of filter substances of candidate compositions tested for their sunscreen performance until the sunscreen performance target is not reachable and by subsequently gradually increase the total amount of filter substances until the performance target is met again, wherein an increment of the gradual increase is smaller than an increment of the gradual reduction.

15. The method as recited in claim 1, comprising the step of providing a list of best candidate compositions.

16. The method as recited in claim 1, comprising the step of optimizing a compromise within a plurality of optimization objectives, comprising the steps of providing acceptable ranges for values relating to each of the objectives, providing relative importance factors between the objectives and minimizing one of the values using the relative importance factors in linear constraints for the minimization.

17. The method as recited in claim 1, comprising the step of automatically determining an optimum solvent composition for the determined sunscreen composition.

18. The method as recited in claim 17, the optimum solvent composition being determined from a minimization of extra solvents under a constraint that all filter substances of a respective sunscreen composition are dissolved.

* * * * *